US009820676B2

(12) United States Patent
Tramm et al.

(10) Patent No.: US 9,820,676 B2
(45) Date of Patent: *Nov. 21, 2017

(54) METHOD AND POSITIONABLE PATIENT-INTERFACE APPARATUS FOR AN MRI SYSTEM

(71) Applicant: Life Services LLC, Minneapolis, MN (US)

(72) Inventors: Brandon J. Tramm, Otsego, MN (US); Matthew T. Waks, Coon Rapids, MN (US); Charles A. Lemaire, Apple Valley, MN (US); Scott M. Schillak, Minneapolis, MN (US)

(73) Assignee: Life Services, LLC, Minneapolis, MN (US)

( * ) Notice: Subject to any disclaimer, the term of this patent is extended or adjusted under 35 U.S.C. 154(b) by 320 days.

This patent is subject to a terminal disclaimer.

(21) Appl. No.: 14/548,276

(22) Filed: Nov. 19, 2014

(65) Prior Publication Data
US 2015/0196226 A1 Jul. 16, 2015

Related U.S. Application Data

(60) Provisional application No. 61/906,409, filed on Nov. 19, 2013.

(51) Int. Cl.
*A61B 5/055* (2006.01)
*G01R 33/34* (2006.01)
(Continued)

(52) U.S. Cl.
CPC ............ *A61B 5/0555* (2013.01); *A61B 5/053* (2013.01); *A61B 5/7405* (2013.01);
(Continued)

(58) Field of Classification Search
CPC ... A61B 2503/06; A61B 5/053; A61B 5/0555; A61B 5/7405; A61B 5/7465; A61J 15/00;
(Continued)

(56) References Cited

U.S. PATENT DOCUMENTS

| 5,449,206 | A | 9/1995 | Lockwood |
| 7,526,330 | B1 * | 4/2009 | Randell ................. A61B 5/055 324/309 |

(Continued)

*Primary Examiner* — Michael Rozanski
(74) *Attorney, Agent, or Firm* — Charles A. Lemaire; Jonathan M. Rixen; Lemaire Patent Law Firm, P.L.L.C.

(57) ABSTRACT

Apparatus and method for imaging a patient in an MRI system. This includes a frame, and at least one assembly that includes a patient-interface positioner connected to a reference position on the frame, a first lockable joint on the positioner; and a patient interface connected to a patient-proximal end of the positioner by a second joint, wherein the first patient-interface is moveably positioned to a selected pitch angle, a selected yaw angle, and a selected one of a plurality of distances relative to the reference position on the frame. The first lockable joint is configured to be tightened to yieldably hold the first patient-interface at the selected pitch and yaw angles, and at the selected one of the plurality of distances, relative to the reference position. Optionally a second substantially similar patient-interface and assembly are provided. The earpiece(s) optionally include audio transducer(s) and/or RF coil(s).

20 Claims, 14 Drawing Sheets

(51) Int. Cl.
*A61J 15/00* (2006.01)
*A61B 5/053* (2006.01)
*A61M 16/00* (2006.01)
*G01R 33/28* (2006.01)
*A61M 21/02* (2006.01)
*A61B 5/00* (2006.01)
*A61M 21/00* (2006.01)

(52) U.S. Cl.
CPC ............. *A61B 5/7465* (2013.01); *A61J 15/00* (2013.01); *A61M 16/00* (2013.01); *A61M 21/02* (2013.01); *G01R 33/28* (2013.01); *G01R 33/283* (2013.01); *G01R 33/34* (2013.01); *A61B 2503/06* (2013.01); *A61M 2021/0027* (2013.01); *A61M 2021/0066* (2013.01); *A61M 2205/3368* (2013.01); *G01R 33/34046* (2013.01); *G01R 33/34084* (2013.01)

(58) Field of Classification Search
CPC .......... A61M 16/00; A61M 2021/0027; A61M 2021/0066; A61M 21/02; A61M 2205/3368; G01R 33/28; G01R 33/283; G01R 33/34; G01R 33/34046; G01R 33/34084

See application file for complete search history.

(56) References Cited

U.S. PATENT DOCUMENTS

| | | | |
|---|---|---|---|
| 8,299,681 | B2 | 10/2012 | Snyder et al. |
| 8,604,791 | B2 | 12/2013 | Vaughan et al. |
| 8,854,042 | B2 | 10/2014 | Vaughan et al. |
| 2006/0149337 | A1 | 7/2006 | John |
| 2011/0166632 | A1 | 7/2011 | Delp et al. |
| 2012/0223709 | A1 | 9/2012 | Schillak et al. |
| 2015/0141803 | A1* | 5/2015 | Tramm ................ A61J 15/00 600/415 |

* cited by examiner

METHOD AND POSITIONABLE PATIENT-INTERFACE APPARATUS FOR AN MRI SYSTEM

CROSS-REFERENCE TO RELATED APPLICATION

This application claims priority benefit, under 35 U.S.C. §119(e), of U.S. Provisional Patent Application No. 61/906,409 filed Nov. 19, 2013 by Brandon J. Tramm, titled "Method and apparatus for adjustable earpieces in an MRI system" (which issued as U.S. Pat. No. 9,700,232 on Jul. 11, 2017), which is incorporated herein by reference in its entirety.

This application is related to U.S. patent application Ser. No. 14/538,635 filed Nov. 11, 2014 by Brandon J. Tramm, titled "Method and apparatus for adjustable earpieces in an MRI system" (which issued as U.S. Pat. No. 9,700,232 on Jul. 11, 2017), (which published as U.S. Application Publication US 2015/0141803 A1 on May 21, 2015), which is incorporated herein by reference in its entirety.

FIELD OF THE INVENTION

This invention relates to the field of mechanical positioners and more specifically to a method and apparatus for adjustable positioning and interfacing in a magnetic-resonance-imaging (MRI) system that can be attached to a head coil (in particular, in systems customized for pediatric imaging), in order to position patient-holding interfaces on a patient for gently restraining the patient to a single position and orientation (optionally including audio headphones for delivery of audio content; while in other embodiments, optionally including RF coils for transmitting and/or receiving RF MRI information, and in other embodiments, optionally including embedded fluid passageways to control temperature (e.g., to cool or warm the tissue of the patient), fluid passageways to deliver liquids to drink and/or gasses to breathe, and/or to hold electrodes against the skin of the patient) and, in some embodiments, mechanisms for adjusting the position and characteristics of the coil (such as RF tuning and impedance matching of the RF coils attached to the ear pieces) electrically and/or mechanically. In some embodiments, a substantially similar unit to the patient-holding interfaces is used to vary the position of RF coils and then yieldably lock the RF coil and/or other interfaces in the desired position and orientation in RF-coil systems and units for other parts of the body besides the head.

BACKGROUND OF THE INVENTION

The problem: During MRI procedures, delivering audio has been cumbersome due to sloppy headphone-to-patient interface provided by conventional headband-type earphones. This conventional device also introduces more foreign objects into the imaging cavity and also increases the distance between the patient and the imaging surface. This reduces the efficiency of the images and increases patient discomfort. These problems are further worsened when performing MRI scans on children. Children typically tend to move around more than adult subjects during scans. Therefore, it is important to deliver sound to occupy the child patient being scanned. It is important to have a large degree of adjustability to accommodate the various ranges of patient ear locations. Movement is also an issue and it is important to restrain the patient's head movements as much as possible without fully restricting an emergency evacuation of the patient from the MRI system.

U.S. Pat. No. 8,854,042, titled "METHOD AND COILS FOR HUMAN WHOLE-BODY IMAGING AT 7 T," filed 5 Aug. 2011 and issued 9 Feb. 2012 to John Thomas Vaughan, Jr. and Charles A. Lemaire, is incorporated herein by reference. U.S. Pat. No. 8,854,042 describes MRI coils for human whole-body MR imaging. A progressive series of five new coils is described. The first coil solves problems of transmit-field inefficiency and inhomogeneity for heart and body imaging, with a close-fitting, 16-channel TEM conformal array design with efficient shield-capacitance decoupling. The second coil progresses directly from the first with automatic tuning and matching, an innovation of huge importance for multi-channel transmit coils. The third coil combines the second, auto-tuned multichannel transmitter with a 32-channel receiver for best transmit-efficiency, control, receive sensitivity and parallel-imaging performance. The final two coils extend the innovative technology of the first three coils to multi-nuclear ($^{31}$P-$^{1}$H) designs to make practical human-cardiac imaging and spectroscopy possible for the first time at 7 T.

U.S. Pat. No. 8,604,791, titled "ACTIVE TRANSMIT ELEMENTS FOR MRI COILS AND OTHER ANTENNA DEVICES," filed 9 Sep. 2010 and issued 10 Dec. 2013 to John Thomas Vaughan, Jr and Charles A. Lemaire, is incorporated herein by reference. This application describes apparatus and method that include amplifiers for transceiver antenna elements, and more specifically to power amplifying an RF (radio frequency) signal using a distributed power amplifier having electronic devices (such as field-effect transistors) that are thermally and/or mechanically connected to each one of a plurality of antenna elements (also called coil elements) to form a hybrid coil-amplifier (e.g., for use in a magnetic-resonance (MR) imaging or spectroscopy machine), and that is optionally adjusted from a remote location, optionally including remotely adjusting its gains, electrical resistances, inductances, and/or capacitances (which controls the magnitude, phase, frequency, spatial profile, and temporal profile of the RF signal)—and, in some embodiments, the components are compatible with, and function in, high fields (such as a magnetic field of up to and exceeding one tesla or even ten tesla or more and/or an electric field of many thousands of volts per meter).

U.S. Patent Application Publication US 2012/0223709 titled "SIMULTANEOUS TX-RX FOR MRI SYSTEMS AND OTHER ANTENNA DEVICES," of U.S. patent application Ser. No. 13/407,751 filed 28 Feb. 2012 by Scott M. Schillak, John Thomas Vaughan, Jr., Charles A. Lemaire and Matthew T. Waks, is incorporated herein by reference. This application (which issued as U.S. Pat. No. 9,097,769 on Aug. 4, 2015) describes an apparatus and a method that are more efficient and flexible, and obtain and connect high-power RF transmit signals (TX) to RF-coil devices in an MR machine or other devices and simultaneously receive signals (RX) and separate net receive signals NRX) of interest by subtracting or filtering to remove the subtractable portion of the transmit signal (STX) from the RX and preamplifying the NRX and signal processing the preamplified NRX. In some embodiments, signal processing further removes artifacts of the transmitted signal, e.g., by digitizing the NRX signal, storing the digitized NRX signal in a memory, and performing digital signal processing. In some embodiments, the present invention also includes pre-distorting the TX signals in order to be better able to identify and/or remove the remaining artifacts of the transmitted signal from the NRX signal. This solution also applies to other high-power RF-transmit-antennae signals.

U.S. patent application Ser. No. 13/831,752 titled "SNAP-ON COAXIAL CABLE BALUN AND METHOD FOR TRAPPING RF CURRENT ON OUTSIDE SHIELD OF COAX AFTER INSTALLATION," filed 15 Mar. 2013 by Matthew T. Waks, Scott M. Schillak and Charles A. Lemaire (which issued as U.S. Pat. No. 9,160,295 on Oct. 13, 2015), is incorporated herein by reference. This application describes an apparatus and a method for a radially attachable RF trap attached from a side to a shielded RF cable. In some embodiments, the RF trap creates a high impedance on the outer shield of the RF cable at a frequency of RF signals carried on at least one inner conductor of the cable. In some embodiments, an RF-trap apparatus for blocking stray signals on a shielded RF cable that has a peripheral shield conductor and an inner conductor for carrying RF signals includes: a case; an LC circuit having a resonance frequency equal to RF signals carried on the inner conductor; projections that pierce and connect the LC circuit to the shield conductor; and an attachment device that holds the case to the cable with the LC circuit electrically connected to the shield conductor of the shielded RF cable.

U.S. Pat. No. 8,299,681 issued to Snyder, et al. on Oct. 30, 2012, titled "Remotely adjustable reactive and resistive electrical elements and method," and is incorporated herein by reference. U.S. Pat. No. 8,299,681 describes an apparatus and method that include providing a variable-parameter electrical component in a high-field environment and based on an electrical signal, automatically moving a movable portion of the electrical component in relation to another portion of the electrical component to vary at least one of its parameters. In some embodiments, the moving uses a mechanical movement device (e.g., a linear positioner, rotary motor, or pump). In some embodiments of the method, the electrical component has a variable inductance, capacitance, and/or resistance. Some embodiments include using a computer that controls the moving of the movable portion of the electrical component in order to vary an electrical parameter of the electrical component. Some embodiments include using a feedback signal to provide feedback control in order to adjust and/or maintain the electrical parameter. Some embodiments include a non-magnetic positioner connected to an electrical component configured to have its RLC parameters varied by the positioner.

U.S. Pat. No. 5,449,206 to Lockwood issued Sep. 12, 1995 titled "Ball and socket joint with internal stop" and is incorporated herein by reference. U.S. Pat. No. 6,042,155 to Lockwood issued Mar. 28, 2000 titled "Ball and socket joint with internal stop" and is incorporated herein by reference. These patents describe a first connector includes opposite ball and socket elements having a passageway formed therethrough. The socket element has a cavity formed therein for receiving a ball element of a second hose connector to form a hose assembly. A ring is disposed within the cavity for limiting pivotal movement of a ball element inserted therein to minimize the risk that the connectors, and thereby the hose assembly, will separate.

U.S. Patent Publication 2011/0166632 by Delp, et al. filed Jul. 8, 2009 with the title "Materials and approaches for optical stimulation of the peripheral nervous system" is incorporated herein by reference. This publication describes methods, devices, systems and arrangements for stimulation of the peripheral nervous system. Consistent with one embodiment of the present invention, method is implemented in which light-responsive channels or pumps are engineered in a set of motor units that includes motor units of differing physical volumes. Optical stimuli are also provided to the light-responsive channels or pumps at an optical intensity that is a function of the size of motor units to be recruited. In certain implementations, the intensity of the optical stimuli is increased so as to recruit increasingly larger motor units.

U.S. Patent Publication 20060149337 by Michael John filed Jan. 20, 2006 with the title "Systems and methods for tissue stimulation in medical treatment" is incorporated herein by reference. This publication describes stimulation treatments for various medical disorders, such as neurological disorders, comprise novel systems, strategies, and methods for providing TMS, electrical, magnetic, optical and other stimulation. Some stimulation methods comprise varying the stimulation parameters to improve the therapeutic efficacy of stimulation, and decrease risk of habituation and side-effects such as interference with normal brain, sensory, motor, and cognitive processes. The creation, and subsequent variation, of stimulation parameters can use sensed data in order to match, adjust, or avoid matching characteristics of the stimulation therapy relative to certain endogenous brain activities. Novel methods are described for choosing, creating and subsequently stimulating with partial signals which summate to produce therapeutic vector fields having unique temporal patterns and low- or high-frequency spectral content.

There is a long-felt need for a method and apparatus for adjustable audio delivery and head restraint in an MRI system.

SUMMARY OF THE INVENTION

The present invention provides a solution: in some embodiments, a 360-degree-plus adjustable cushioned patient-restraining patient interface pieces integrated into an MRI coil. In some embodiments, the MRI coil is a pediatric head coil. In some other embodiments, the MRI coil is a head coil for adults. In some embodiments, the adjustable cushioned head-restraining ear pieces include an audio-delivery system integrated into the MRI coil.

In some embodiments, the patient-restraining patient interface pieces include audio transducers. The adjustable cushioned audio system is designed to be used, in some embodiments, with a wide array of pre-existing audio headphones. In some embodiments, the design of the present invention includes of a series of ball-and-socket mechanisms that can be adjusted 360 degrees (in a combination of pitch and yaw relative to the longitudinal axis of the headphone-positioning rod) as well as in-and-out along the longitudinal axis of the headphone-positioning rod, and rotation around the longitudinal axis of the headphone-positioning rod in a roll direction, and then tightened in the proper position. In some embodiments, the earpieces are affixed to the proximal end of the headphone-positioning rods using a ball-and-socket joint that facilitates orienting the earpieces to conform to the sides of the patient's head. The system is modular in design and can be integrated into other MRI coil housings with slight modifications to those housings and/or the parts as described herein. In some embodiments, the system is designed with standard tapered threading on the ball-holding units. This allows an operator to apply increased friction between moving parts to firmly lock or snug them securely in place by tightening the locking collars, while the friction can be overcome to release the patient in an emergency. The system also acts as a dual-purpose adjustable head-constraining and/or—restraining device that can be used with or without audio being supplied, in that the cushioned head pieces are implemented without audio generation in some embodiments.

In other embodiments, the present invention includes a positionable cushioned patient-interface assembly having RF coils, automatic tune-and-match circuitry to tune the resonant frequency of the coils, a fluid-circulation system to control temperature at the skin surface, a system to deliver liquids to drink and/or gasses to breathe and/or drugs and/or anesthesia liquids and/or gasses, electrodes to stimulate and/or detect nerve-action potentials and/or other physiological signals. In some embodiments, the positionable cushioned patient-interface assembly includes one or more RF power amplifiers to amplify RF signals to be transmitted from RF coils in the positionable cushioned patient-interface assembly and/or one or more RF preamplifiers to amplify RF signals that have been received by the RF coils.

DESCRIPTION OF PREFERRED EMBODIMENTS

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

As used herein, a non-magnetic mechanical-movement device is any electrically-controlled device (such as a linear positioner, rotary motor, or pump) made of materials that do not move (or move to a substantially negligible amount) due to a high magnetic field when subjected to the high magnetic field. Such devices can be placed within the high magnetic field of a magnetic-resonance machine or the superconducting magnet of a particle accelerator without the danger of the device moving due to the magnetic field and/or without the undesirable result of changing the magnetic field due to their presence. In many of the descriptions herein, the term "motor" (such as motor 1240) will be used as an example of such a non-magnetic mechanical movement device, however one of skill in the art will recognize that in other embodiments, the "motor" can be implemented as a linear or rotary motor device using suitable linkages, or as a pump that uses a liquid or pneumatic fluid to effectuate the described movement.

Figure 1:
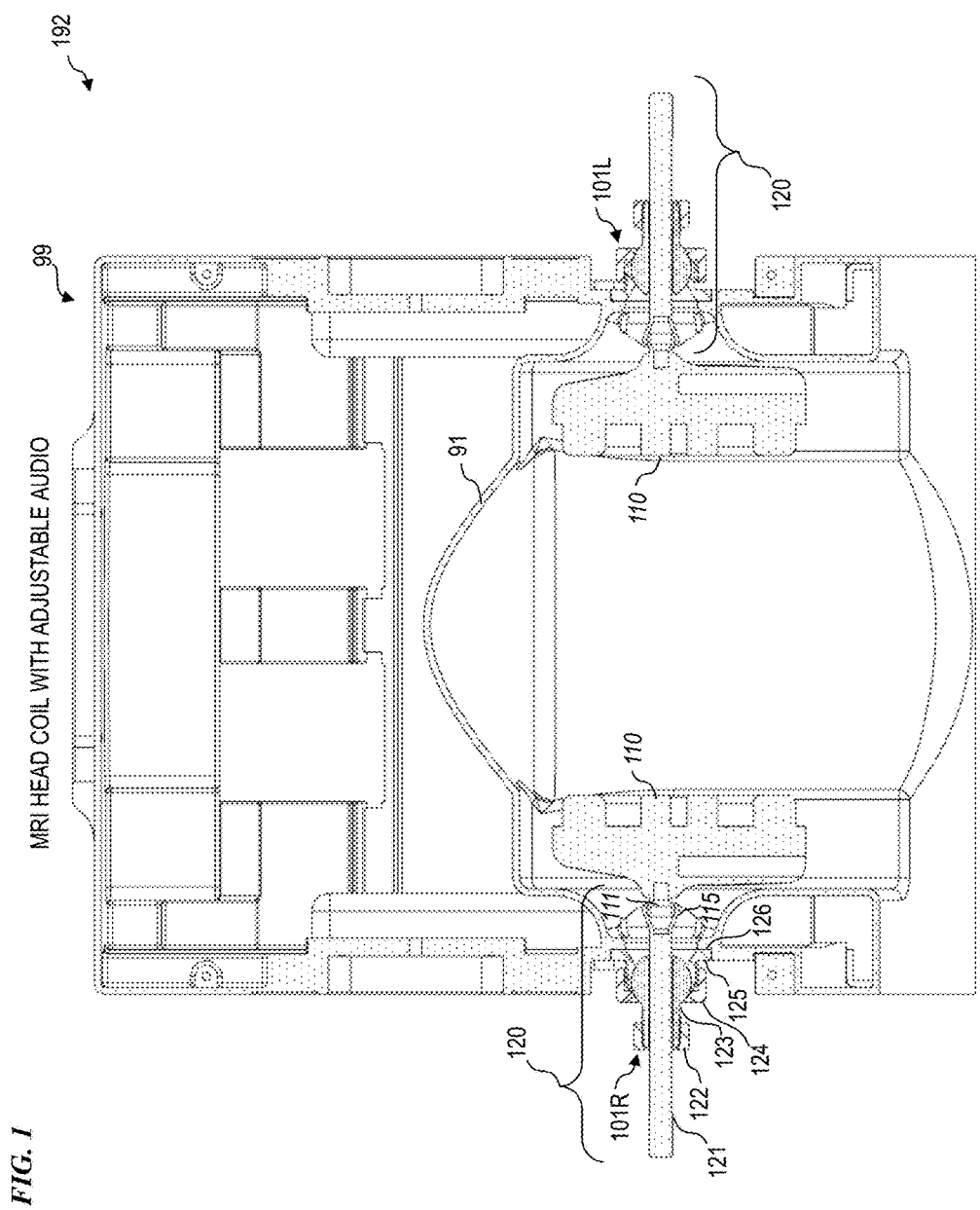
FIG. 1 is a plan-view cross-sectional drawing of a head-coil system 192 that uses two adjustable cushioned earpiece assemblies 101R and 101L, according to some embodiments of the present invention.

FIG. 1 is a plan-view cross-sectional drawing of a head-coil system 192 that uses two adjustable cushioned earpiece assemblies 101R and 101L, according to some embodiments of the present invention. The present invention includes or is used with an MRI head coil 99. In some embodiments, head coil 99 is sized for pediatric-patient use, including infants, children or small adults. Such patients are often fearful, fidgety, and restless, and the earpiece assemblies (e.g., 101L and 101R in FIG. 1, 701 in FIGS. 7A, 7B, 8 and 9) help to hold the patient's head in a fixed location. In some embodiments, head coil 99 is of a conventional adult-head size. In some embodiments, the earpiece assemblies 101L, 101R, and/or 701 include audio transducers for providing audio to the patient. In some other embodiments, the earpiece assemblies 101L, 101R, and/or 701 receive audio delivered through plastic tubing connected to the earpiece, where the audio is from one or more remote audio transducers.

In some embodiments, each of the assemblies 101R and 101L includes a cushioned earpiece 110 and an earpiece-position-adjustment assembly 120. In some embodiments, each earpiece-position-adjustment assembly 120 includes a tightenable ball-and-socket joint that includes ball unit 123, and a tightenable socket assembly that includes a female-threaded socket portion 124 and a male-threaded socket portion 125. In some embodiments, the male-threaded socket portion 125 is attached to head-coil recess 126 (e.g., in some embodiments, using polymer screws, while in other embodiments, adhesives or other fastening means are used). Tightening female-threaded socket portion 124 to male-threaded socket portion 125 releasably locks the pitch-and-yaw orientation of ball unit 123. By partially tightening female-threaded socket portion 124 to male-threaded socket portion 125, a sufficient force applied from the head of the patient will overcome the friction lock and allow the pitch-and-yaw orientation to move, for example, for patient comfort or emergency extraction of the patient from the restraint. In some embodiments, ball unit 123 has a slotted male-thread portion that clamps on rod 121 to restrain the in-and-out motion of rod 121 when female-threaded nut 122 is tightened. In some embodiments, a further ball-and-socket joint is provided at the end of the rod that is proximal to earpiece 110; for example, in some embodiments, by ball 111 and socket 115. In some embodiments, each earpiece 110 includes an audio delivery system that provides audio to the patient to calm and/or entertain the patient and/or communicate from the operator to the patient. In other embodiments, each earpiece 110 is used to just restrain head movement of the patient and omits the audio delivery system. In some embodiments, the pieces of earpiece-position-adjustment assembly 120 are made of a polymer, such as for example, a polycarbonate (e.g., Lexan® or the like). In some embodiments, the tightenable female-threaded socket portion 124 and nut 122 are faceted (e.g., with a standard nut-faces in a hexagonal pattern), or have finger-tightenable wings (such as used in wing nuts) or the like.

Figure 2:
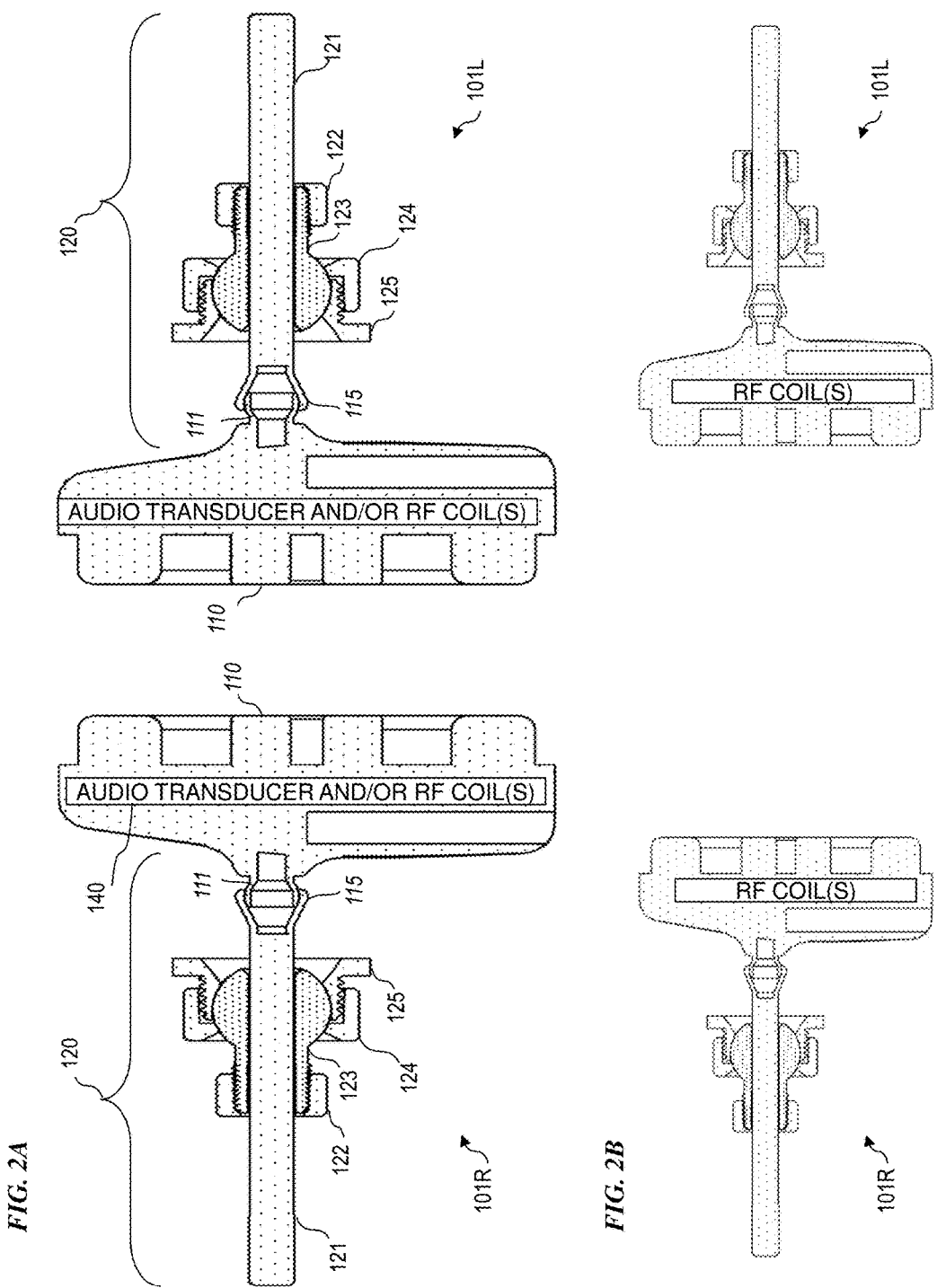
FIG. 2A is a plan-view cross-sectional drawing of two adjustable cushioned head-piece assemblies 101R and 101L, according to some embodiments of the present invention.
FIG. 2B is another plan-view cross-sectional drawing of two adjustable cushioned head-piece assemblies 101R and 101L, according to some embodiments of the present invention.

FIG. 2A is a plan-view cross-sectional drawing of two adjustable cushioned earpiece assemblies (also called, more generically, positionable cushioned patient interface assemblies) 101R and 101L, according to some embodiments of the present invention. The various parts of cushioned earpiece assemblies 101R and 101L are described above in the discussion of FIG. 1. In some embodiments, assembly 140 in each positionable cushioned patient-interface assembly 101R and 101L includes one or more audio transducers. In some embodiments, assembly 140 in each positionable cushioned patient-interface assembly 101R and 101L includes one or more RF coils for transmitting and/or receiving RF signals for the MRI process. In some embodiments, each positionable cushioned patient-interface assembly 101R and 101L includes one or more RF power amplifiers for the transmit signals. In some embodiments, each positionable cushioned patient-interface assembly 101R and 101L includes one or more RF preamplifiers for the receive signals.

FIG. 2B is another plan-view cross-sectional drawing of two adjustable cushioned head-piece assemblies 101R and 101L, according to some embodiments of the present invention. The various parts of cushioned earpiece assemblies 101R and 101L are described above in the discussion of FIG. 1.

Figure 3:
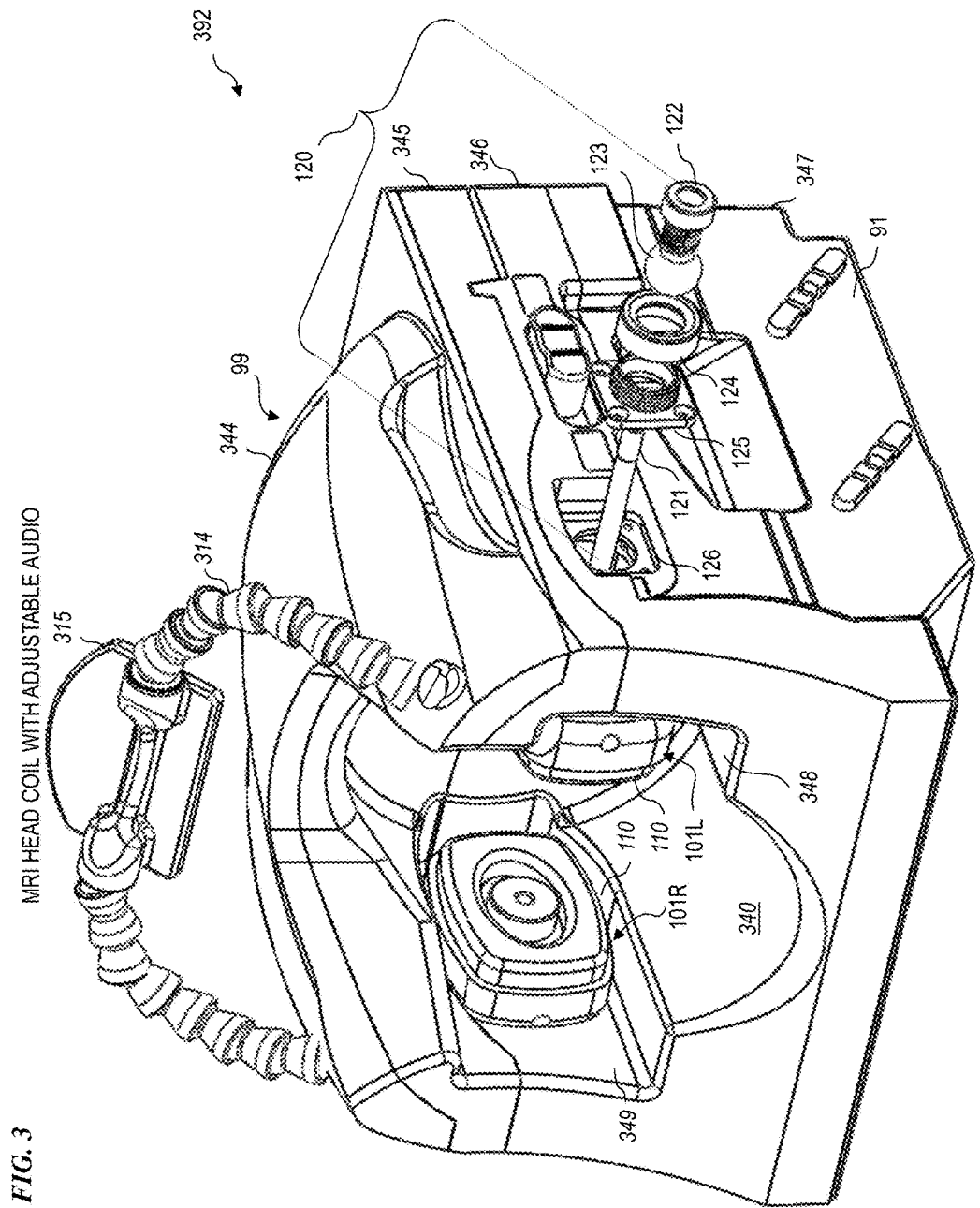
FIG. 3 is a perspective-view partially exploded drawing of a head-coil system 392 that uses two adjustable cushioned head-piece assemblies 101R and 101L, according to some embodiments of the present invention.

FIG. 3 is a perspective-view partially exploded drawing of a head-coil system 392 that uses two adjustable cushioned head-piece assemblies 101R and 101L, according to some embodiments of the present invention. The various parts of cushioned earpiece assemblies 101R and 101L are described above in the discussion of FIG. 1. Many of the various parts of cushioned earpiece assemblies 101R and 101L are described above in the discussion of FIG. 1. Additionally, in contrast to head-coil system 192, some embodiments of head-coil system 392 include a minor 315 (for delivering visual information to the patient) that is positionable and repositionable to a variety of locations and orientation angles using plastic flexible-piping units 314 that are stiff enough to hold minor 315 in the position fixed by an operator of the system. In some embodiments, flexible-piping units 314 include Loc-Line modular hose pieces such as are available from Lockwood Products, Lake Oswego, Oreg. (or described in U.S. Pat. Nos. 6,042,155 and 5,449,206, which are incorporated herein by reference). In some embodiments, the proximal end of rod 121 and its mating connector on earpiece 110 include Loc-Line modular connector pieces such as are available from Lockwood Products, Lake Oswego, Oreg. (or described in U.S. Pat. Nos. 6,042,155 and 5,449,206, which are incorporated herein by reference). In some embodiments, head coil 99 includes a top coil piece 344 which connects to the other coil pieces 345, 346 and 347. In some embodiments, at a suitable location on coil face 91, a receptacle 126 is formed to receive the base of male-threaded socket portion 125. In some embodiments, head coil 99 includes a left-hand-side recess 348 and a right-hand-side recess 349 that are sized to provide adequate clearance for earpieces 110, in order that the earpieces 110 can be moved into proper position against the ears of the patients as may be encountered in different locations due to different-sized heads. In some embodiments, rods 121 are manually moved by the MRI operator to the desired/proper positions, and then the angle is fixed by tightening nut 124 and the depth to the patient's ear is fixed by tightening nut 122. In some embodiments, these two nuts provide a suitable amount of friction to hold rod in place up to a certain predetermined amount of applied force, but the friction will allow the angle and/or depth to be changed by an excess or additional amount of force, in order to release the patient in emergencies. Head coil 99 includes a head rest surface 340 that supports the back of the patient's head.

Figure 4:
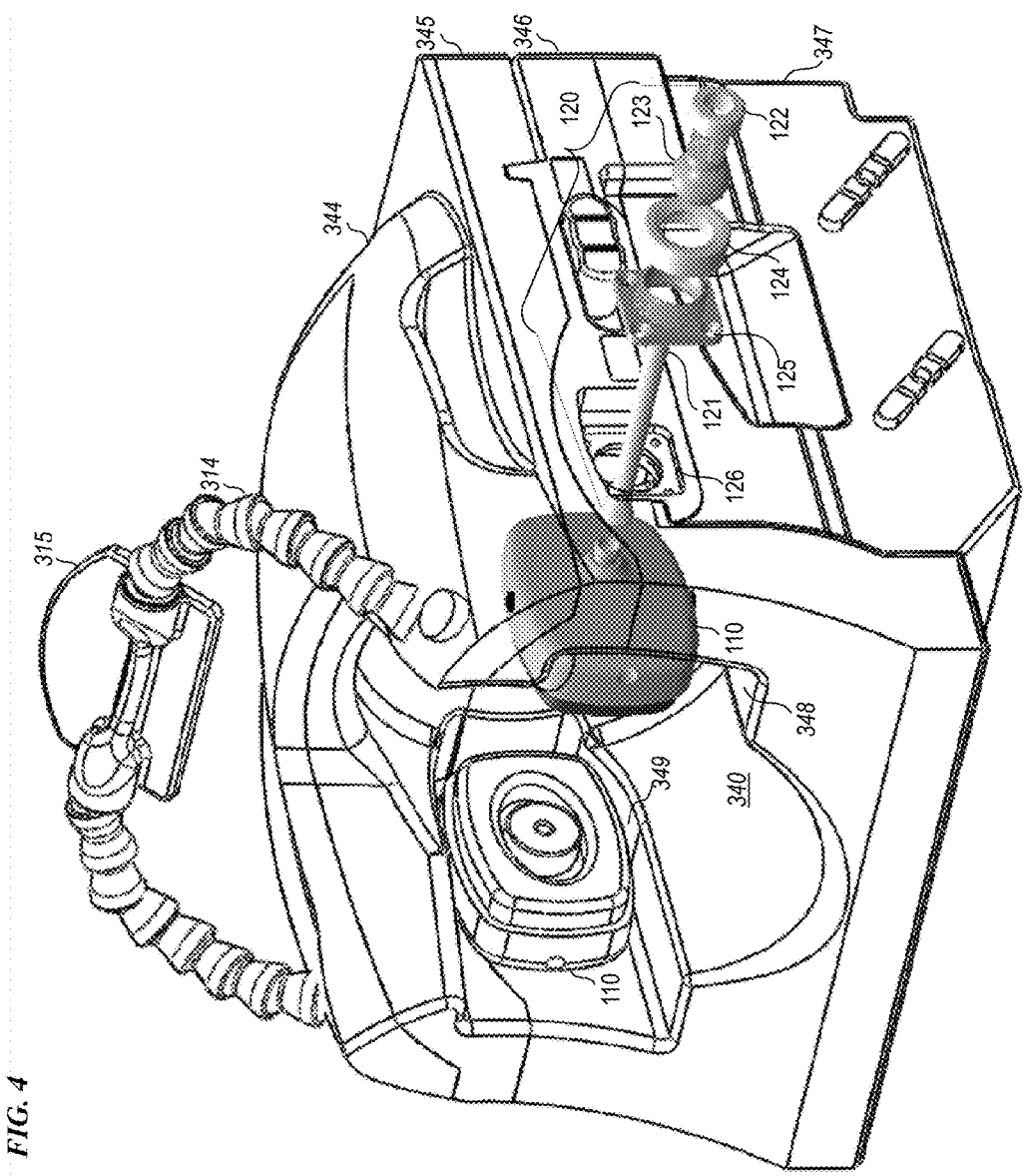
FIG. 4 is a perspective-view partially exploded and partially transparent drawing of a head-coil system 392 that uses two adjustable cushioned head-piece assemblies 101R and 101L, according to some embodiments of the present invention.

FIG. 4 is a perspective-view partially exploded and partially transparent drawing of a head-coil system 192 that uses two adjustable cushioned head-piece assemblies 101R and 101L, according to some embodiments of the present invention. The various parts shown in FIG. 4 are described above in the discussion of FIGS. 1-3.

Figure 5:
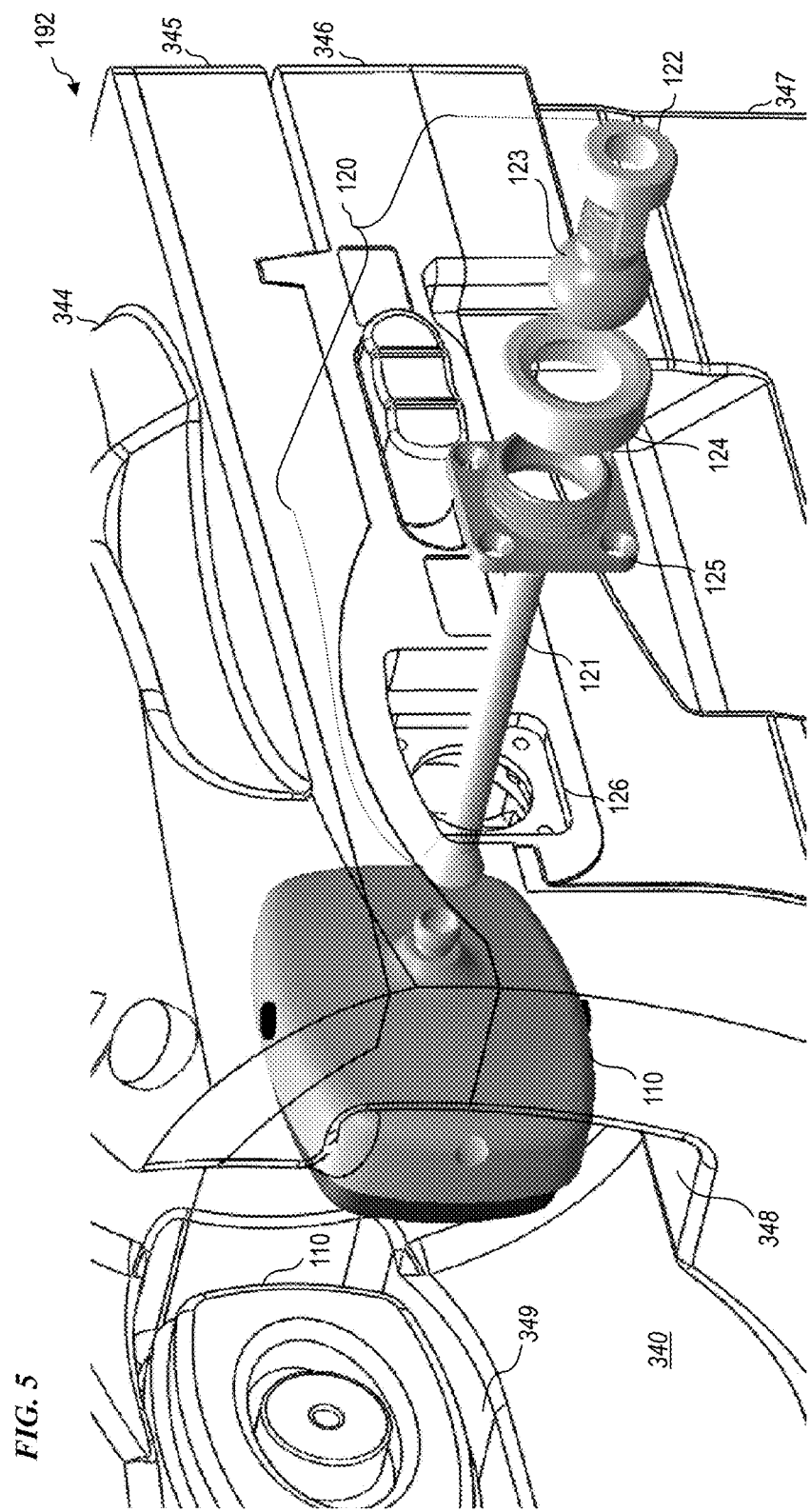
FIG. 5 is an enlarged portion of a perspective-view partially exploded and partially transparent drawing of a head-coil system 192 that uses two adjustable cushioned head-piece assemblies 101R and 101L, according to some embodiments of the present invention.

FIG. 5 is an enlarged portion of a perspective-view partially exploded and partially transparent drawing of a head-coil system 192 that uses two adjustable cushioned head-piece assemblies 101R and 101L, according to some embodiments of the present invention. The various parts shown in FIG. 5 are described above in the discussion of FIGS. 1-3.

Figure 6:
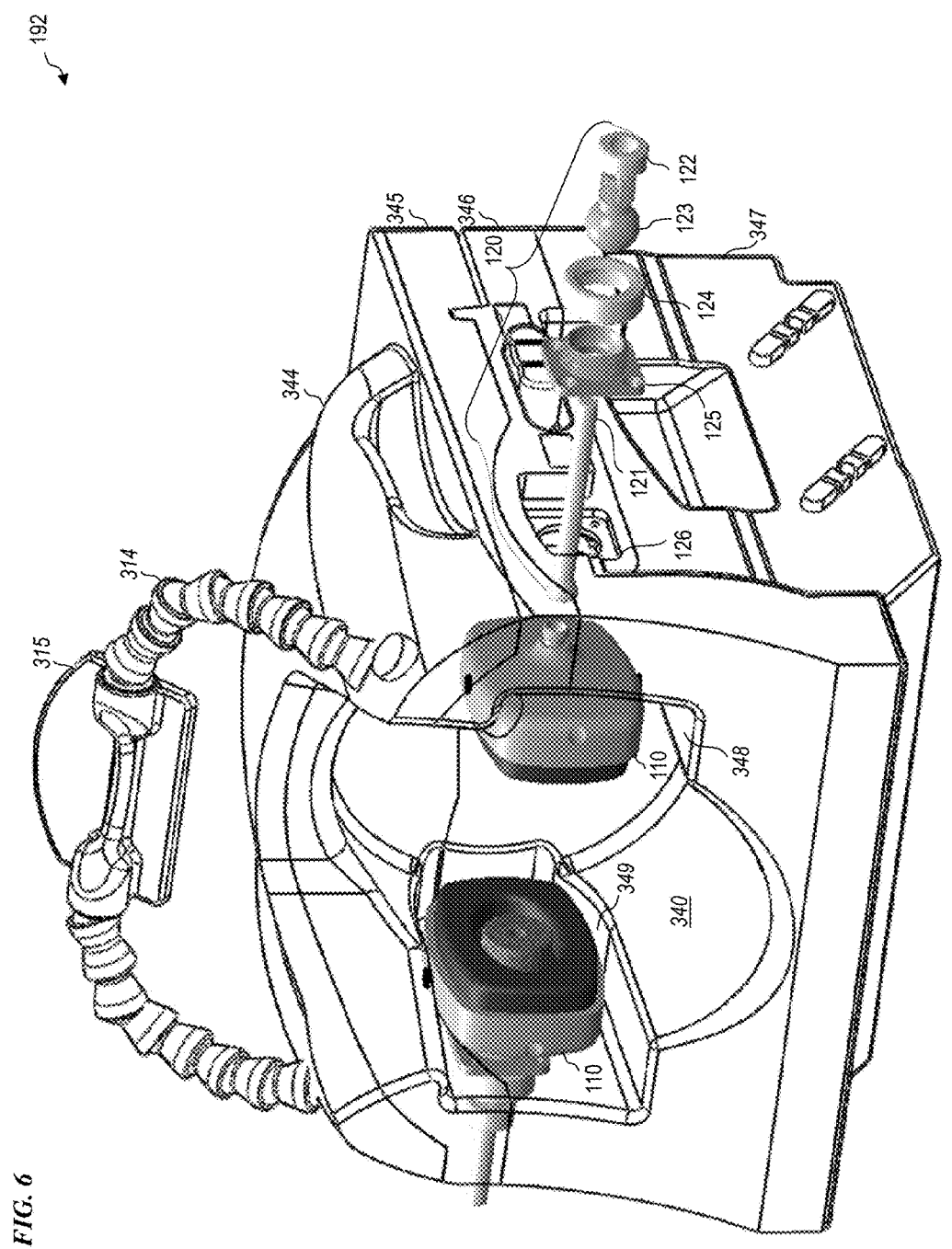
FIG. 6 is a perspective-view partially exploded and partially transparent drawing of a head-coil system 392 that uses two adjustable cushioned head-piece assemblies 101R and 101L, according to some embodiments of the present invention.

FIG. 6 is a perspective-view partially exploded and partially transparent drawing of a head-coil system 192 that uses two adjustable cushioned head-piece assemblies 101R and 101L, according to some embodiments of the present invention. The various parts shown in FIG. 6 are described above in the discussion of FIGS. 1-3.

Figure 7A:
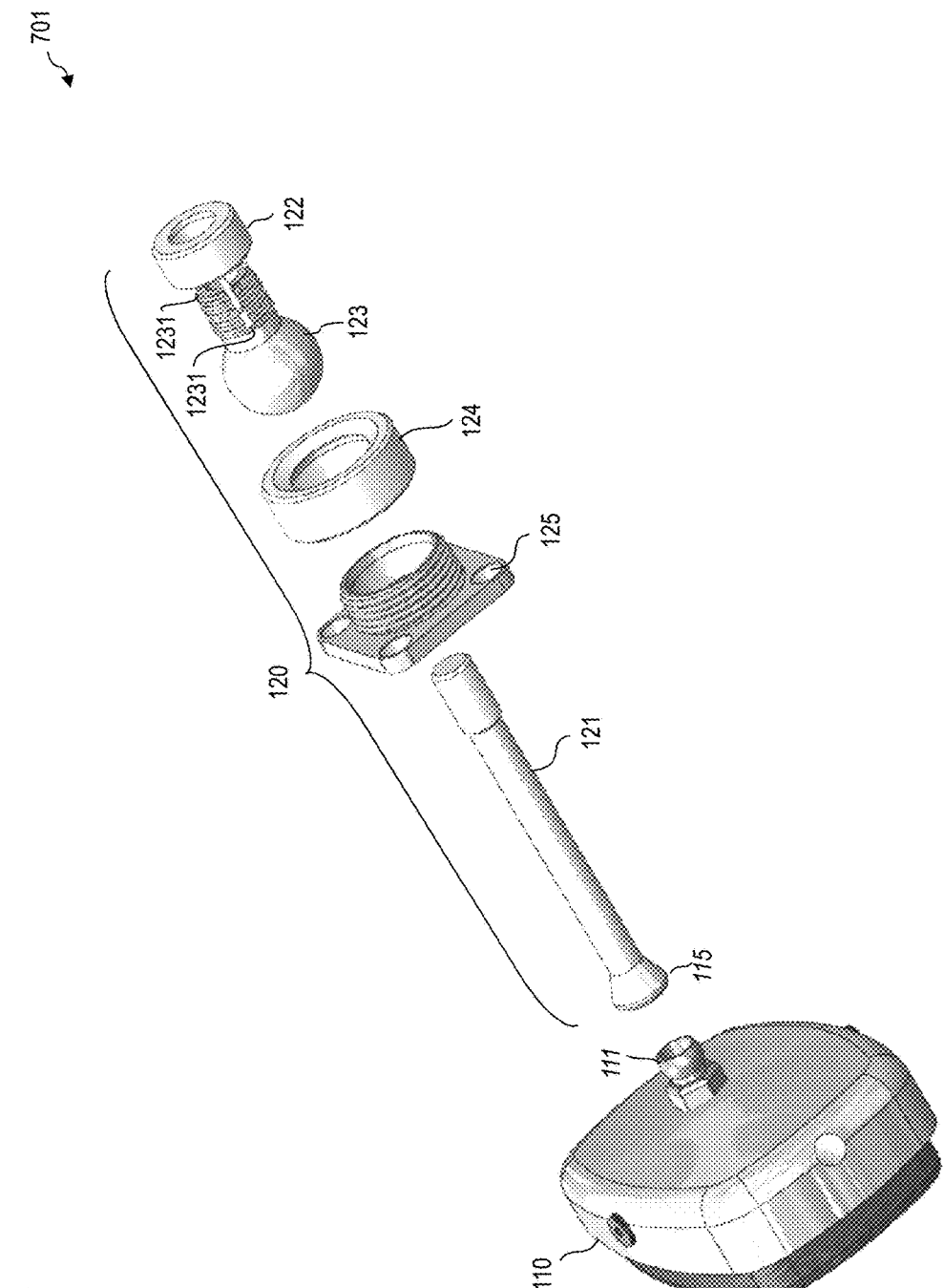
FIG. 7A is an exploded perspective-view drawing an adjustable cushioned head-piece assembly 701, according to some embodiments of the present invention.

FIG. 7A is an exploded perspective-view drawing an adjustable cushioned head-piece assembly 701, according to some embodiments of the present invention. The various parts shown in FIGS. 7A and 7B are described above in the discussion of FIGS. 1-3.

Figure 7B:
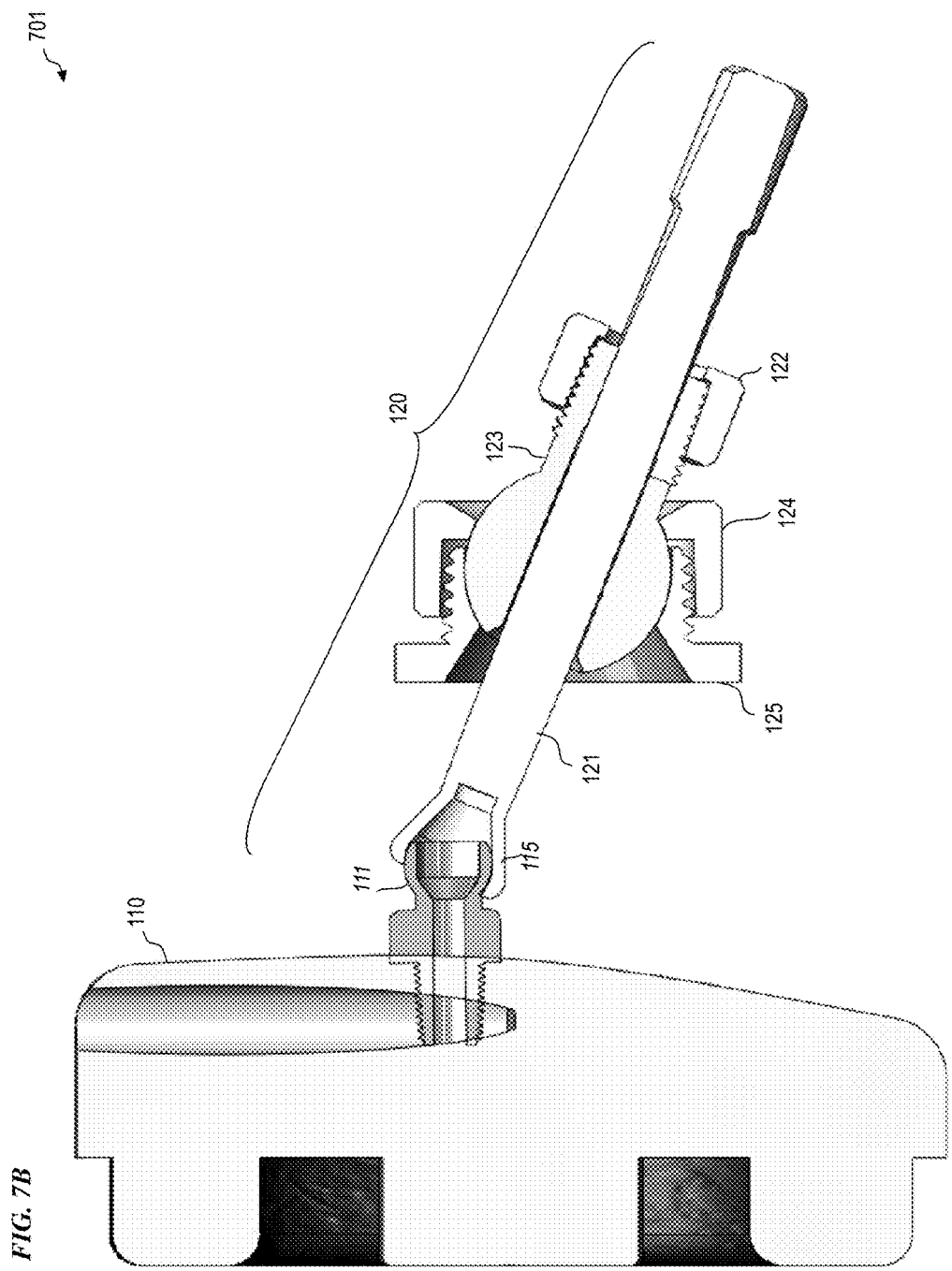
FIG. 7B is a plan-view cross-sectional of adjustable cushioned head-piece assembly 701, according to some embodiments of the present invention.

FIG. 7B is a plan-view cross-sectional of adjustable cushioned head-piece assembly 701, according to some embodiments of the present invention.

Figure 8A:
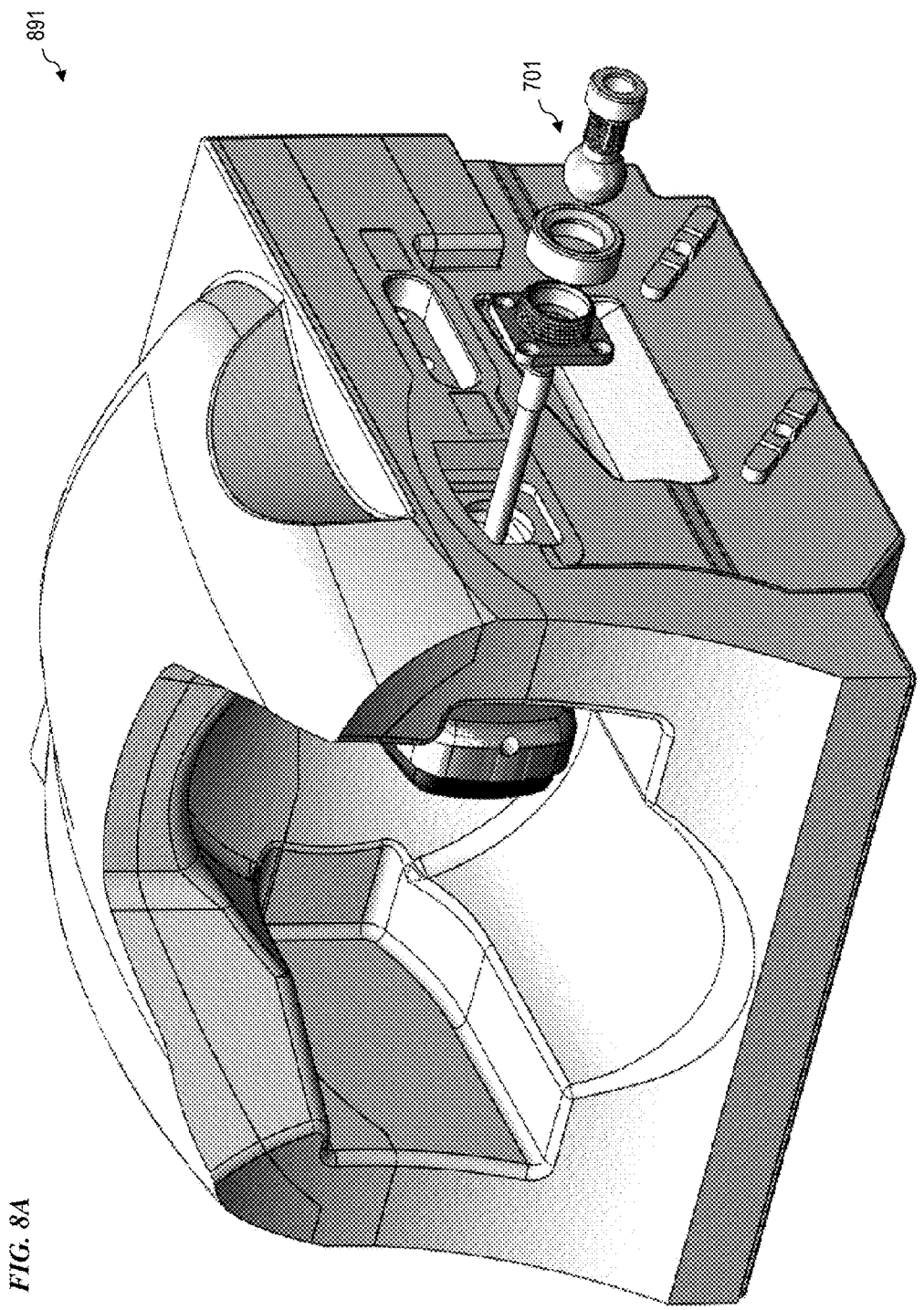
FIG. 8A is a perspective-view drawing of a head-coil system 891 that uses one adjustable cushioned head-piece assembly 701, according to some embodiments of the present invention.
Figure 8B:
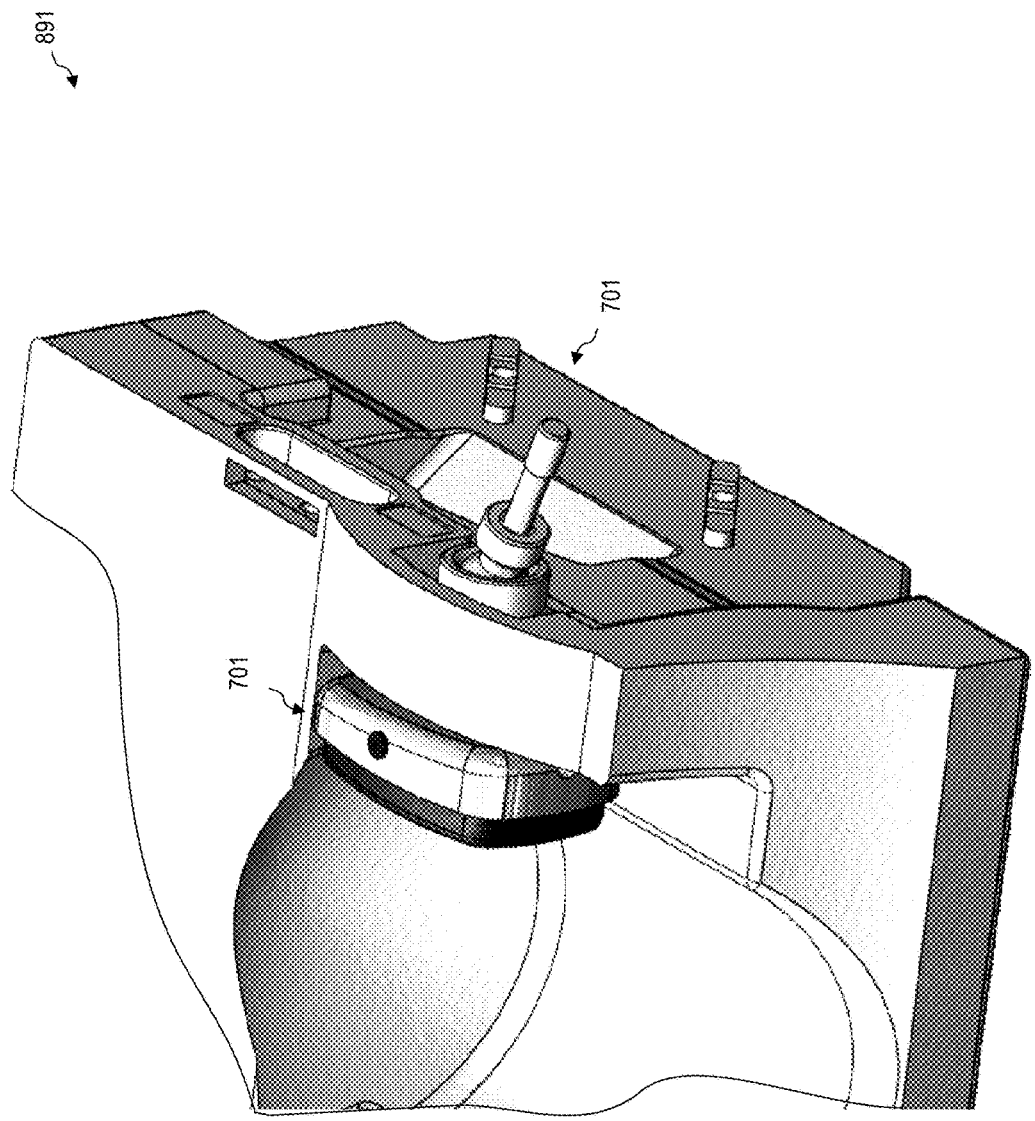
FIG. 8B is a perspective-view drawing of a portion of head-coil system 891 that uses one adjustable cushioned head-piece assembly 701, according to some embodiments of the present invention.

FIG. 8A is a perspective-view drawing of a head-coil system 891 that uses a single adjustable cushioned head-piece assembly 701, according to some embodiments of the present invention. The various parts shown in FIG. 8A and FIG. 8B are described above in the discussion of FIGS. 1-3 and 7A-7B. In some embodiments, the single adjustable cushioned head-piece assembly 701 holds only one side of the head of the patient, while the opposite side can be supported or cushioned in a conventional manner such as by using a pillow. This may be better suited for patients with various types of head trauma or disease. In some embodiments, the head-piece assembly 701 for the side opposite the single remaining assembly 701 is simply removed by loosening both nuts 122 and 124 (and, depending on the embodiment, by removing a rubber tip or other attachment at the distal end of rod 121) and pulling the assembly 701 toward the middle of head coil 891. (Note that in FIG. 8A, a cover has been placed over receptacle 126 on the far side of the coil 891.)

FIG. 8B is another perspective-view drawing of a portion of head-coil system 891 that uses one adjustable cushioned head-piece assembly 701, according to some embodiments of the present invention.

Figure 9:
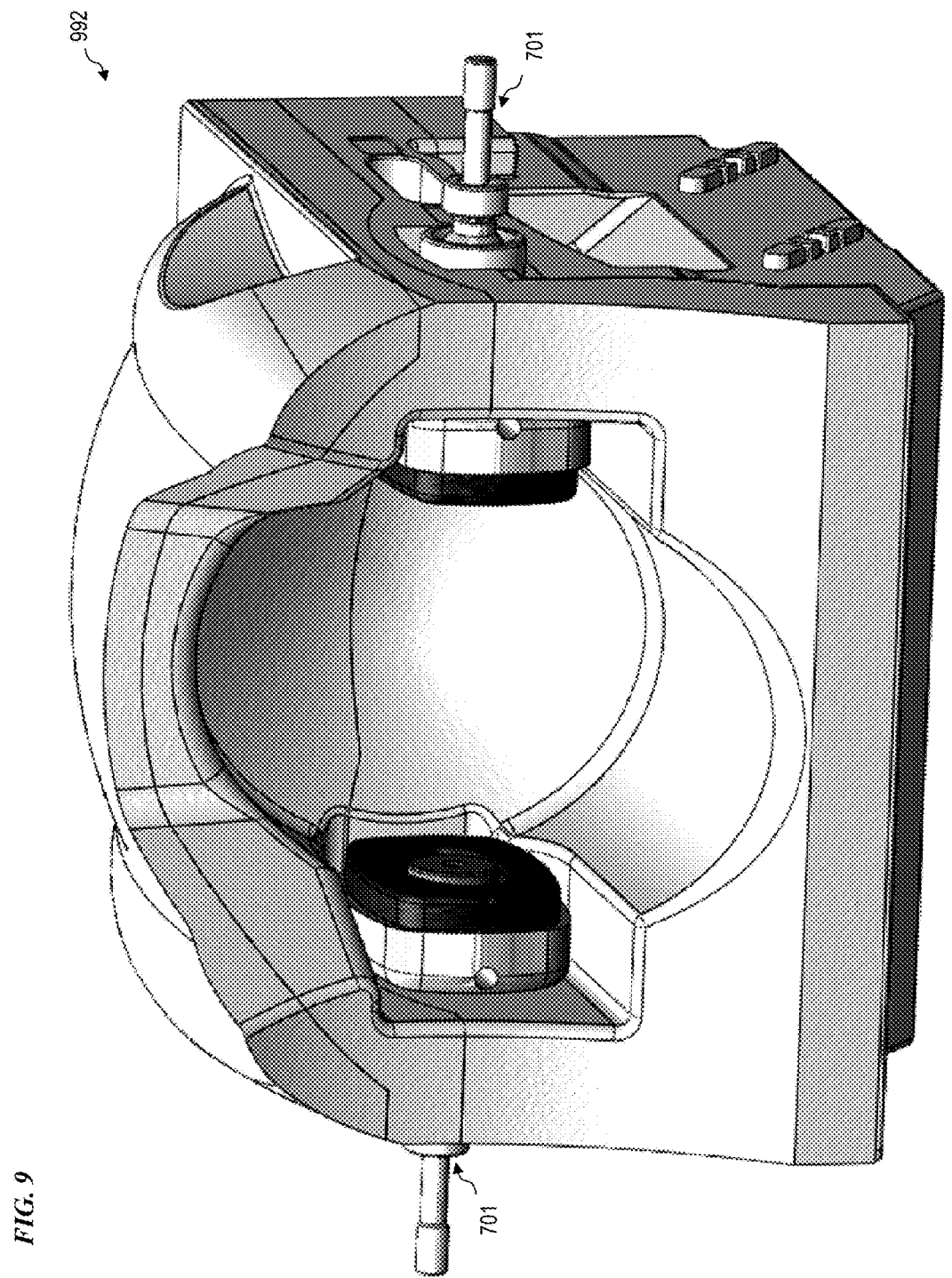
FIG. 9 is a perspective-view drawing of head-coil system 992 that uses two adjustable cushioned head-piece assemblies 701, according to some embodiments of the present invention.

FIG. 9 is a perspective-view drawing of head-coil system 992 that uses two adjustable cushioned head-piece assemblies 701, according to some embodiments of the present invention. The various parts shown in FIG. 9 are described above in the discussion of FIGS. 1-3 and 7A-7B. In some embodiments, head-coil system 992 omits the visual-stimulation assembly (e.g., minor 315 of FIG. 3 is omitted).

Figure 10:
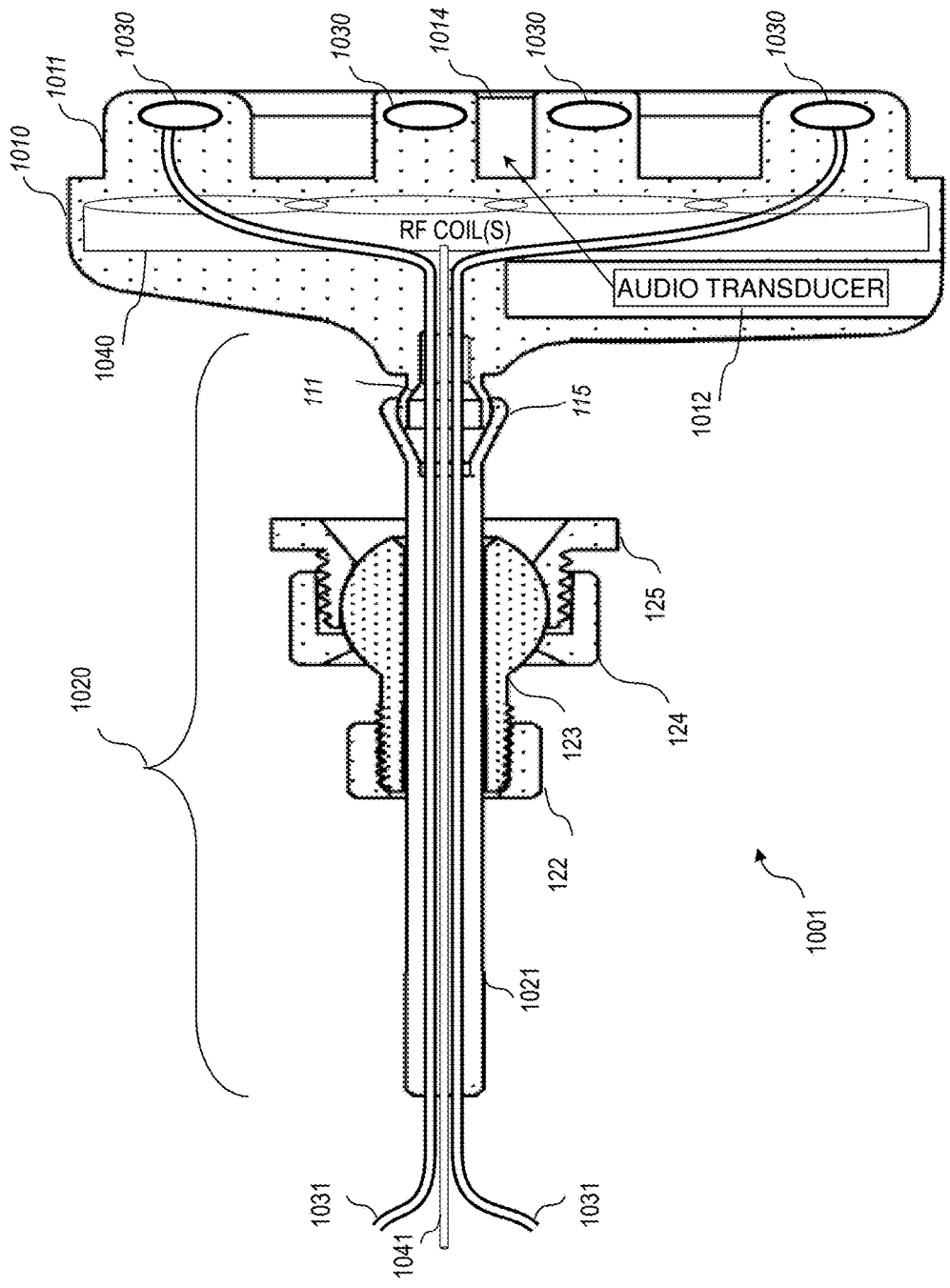
FIG. 10 is a plan-view cross-sectional drawing of a positionable cushioned patient-interface assembly 1001, according to some embodiments of the present invention.

FIG. 10 is a plan-view cross-sectional drawing of a positionable cushioned patient-interface assembly 1001, according to some embodiments of the present invention. The various parts of positionable cushioned patient-interface assembly 1001 are described above in the discussion of FIG. 1. In some embodiments, assembly 1012 in positionable cushioned patient-interface assembly 1001 includes one or more audio transducers configured to output sound to the patient through earhole 1014. In some embodiments, assembly 1040 in positionable cushioned patient-interface assembly 1001 includes one or more RF coils for transmitting and/or receiving RF signals for the MRI process. In some embodiments, positionable cushioned patient-interface assembly 1001 includes one or more RF power amplifiers (see block 1161 of FIG. 11) for the transmit signals. In some embodiments, positionable cushioned patient-interface assembly 1001 includes one or more RF preamplifiers (see block 1162 of FIG. 11) for pre-amplifying the weak receive signals. In some embodiments, one or more co-axial cables 1041 deliver RF signals to be transmitted and optionally power for the RF power amplifiers and/or RF preamplifiers from the MRI console (not shown here, but well known in the art) to the positionable cushioned patient-interface assembly 1001, and the received RF signals from positionable cushioned patient-interface assembly 1001 that are sent back out to the MRI console. In some embodiments, a hollow rod 1021 is used for getting the cables from outside and going into interface housing 1010. In some embodiments, interface housing 1010 includes cushions 1011 for patient comfort as interface housing 1010 of positionable cushioned patient-interface assembly 1001 is pressed against the tissue of the patient being examined. In some embodiments, interface housing 1010 includes a passageway 1030 (e.g., serpentine or helical or other suitable topology, where here the cross-sectional openings for four portions of a single passageway 1030 (which extends from the connection at the top of the upper tube 1031 to the bottom of the lower tube 1031) are shown) for circulating fluids that are supplied from one input/output tube 1031 and returned through the other input/output tube 1031. The fluids circulating in passageway 1030 are used for temperature control (e.g., in some embodiments, to cool the patient and remove at least some of the heat deposited in the patient's tissue by the RF signal (and, in certain circumstances, power from the gradient field coils (not shown here, but well known in the art). In some embodiments, the tubing 1031 and the RF coax 1041 are flexible such that they bend as needed as they cross between end 115 of rod 1021 and the received 111 of housing 1010. Other parts are as described above for FIG. 1 and FIG. 2A.

Figure 11:
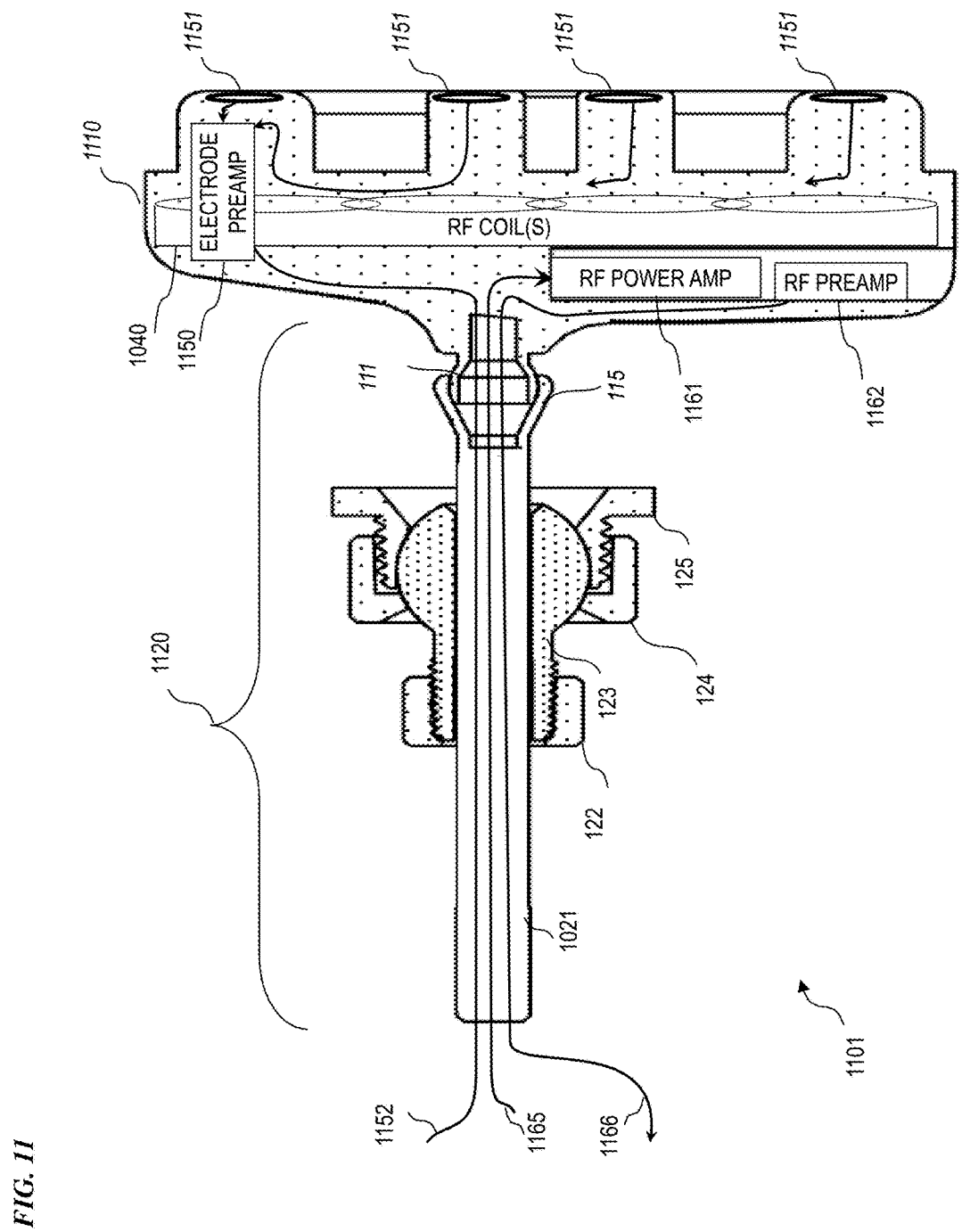
FIG. 11 is a plan-view cross-sectional drawing of a positionable cushioned patient-interface assembly 1101, according to some embodiments of the present invention.

FIG. 11 is a plan-view cross-sectional drawing of a positionable cushioned patient-interface assembly 1101, according to some embodiments of the present invention. In some embodiments, positionable cushioned patient-interface assembly 1101 includes some or all of the features of positionable cushioned patient-interface assembly 1001 (FIG. 10) and/or includes some or all of the features of positionable cushioned patient-interface assembly 1201 (FIG. 12), as well as some or all of the features shown in FIG. 11. In some embodiments, positionable cushioned patient-interface assembly 1101 includes a rod 1021 that has embedded within it one or more electrical power conductors and/or one or more signal conductors (which, in some embodiments, are either electrical conductors or optical fibers or both for transmitting (e.g., signal conductor 1165) or receiving (e.g., signal conductor 1166) or both transmitting and receiving (e.g., signal conductor 1151) signals). In some embodiments, signals on conductor 1152 (which can be electrical, optical, or both) are used to either stimulate the patient's tissue or detect signals from the patient's tissue or both stimulate and detect signals in the tissue. In some embodiments, a plurality of skin-interface electrodes 1151 is connected to electrode preamplifier 1150. In other embodiments, rather than electrodes and electrical signals, an optical fiber interface to the patient's tissue is used to convey optical signals to or from the patient (e.g., such as described in U.S. Patent Publication 2011/0166632 by Delp, et al. and/or U.S. Patent Application Publication 2006/0149337 A1 by John).

Figure 12:
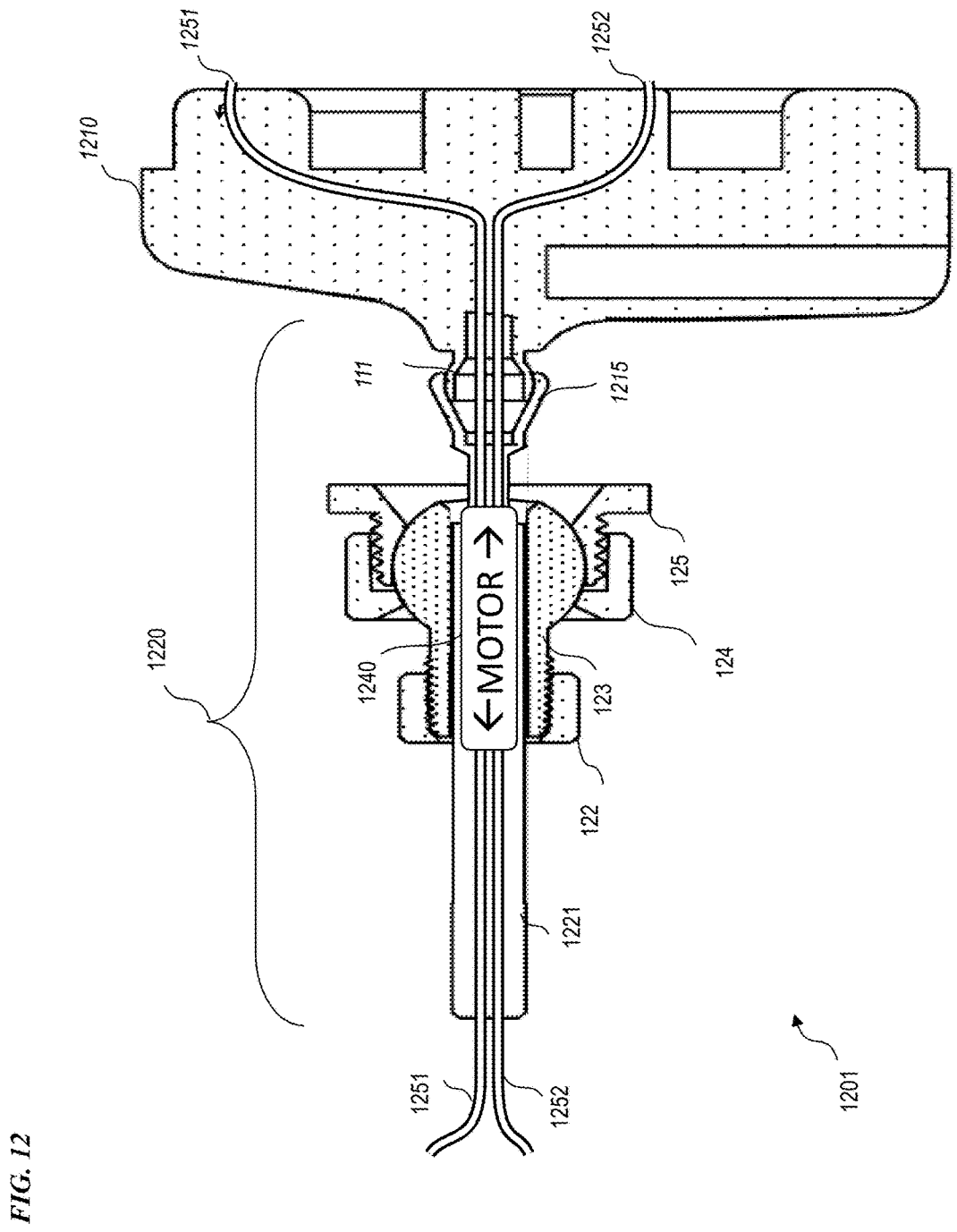
FIG. 12 is a plan-view cross-sectional drawing of a positionable cushioned patient-interface assembly 1201, according to some embodiments of the present invention.

FIG. 12 is a plan-view cross-sectional drawing of a positionable cushioned patient-interface assembly 1201, according to some embodiments of the present invention. In some embodiments, assembly 1201 includes a motor 1240 that can be activated from the remote console to extend or retract the housing 1210 toward or away from the patient during the MRI procedure without the need for an operator to approach the MRI magnet or the patient. In some embodiments, motor 1240 is affixed within rod 1221, and includes a linear actuator that extends or withdraws the socket end 1215 relative to the left end of rod 1221. In addition or alternatively, some embodiments include delivery tubes 1251 and/or 1252 for delivering liquids or gasses to the patient (e.g., in some embodiments, to drink or smell for fMRI (functional MRI) procedures; in other embodiments, pharmaceuticals or anesthetics can be administered to the patient during the procedure.

Note that in some embodiments, any feature described or shown herein (e.g., all of FIGS. 1-12) can be and are combined with one or more other features described or shown herein. For simplicity and ease of understanding, fewer than all features possible are shown in each Figure.

In some embodiments, a positionable cushioned patient-interface assembly of the present invention (e.g., any of FIGS. 1-12) can be used within a frame for positioning, holding and/or pressing against other body parts, such as wrist, ankle, knee, shoulder, hip or other body part.

In some embodiments, the system of the present invention includes a rod connected to a head coil by a lockable ball joint, and an earpiece connected to the rod by another ball joint.

In some embodiments, the one or more non-magnetic (e.g., piezoelectric) motors actuate control over electrical switches, amplitude modulators, frequency controllers, phase controllers, gain controllers, frequency modulators and the like by using, for example, control of variable resistor(s), inductor(s), capacitor(s), antenna(s), dielectric shape(s), mechanical positioner(s) and the like.

In some embodiments, the system uses non-magnetic (e.g., piezoelectric) motors (or other mechanical-movement devices) that include linear actuators, rotary actuators, pumps (pneumatic (pressure or vacuum) and/or liquid pumps) and/or the like. In some embodiments, the system optionally includes non-magnetic sensors (e.g., using piezoelectric or other suitable technologies) that include linear strain gauges, rotary sensors, pressure or sound sensors (e.g., pneumatic (pressure or vacuum) and/or liquid), position sensors, light and image sensors, voltage or current sensors, and/or the like. In some embodiments, such actuator elements and/or sensor elements are used for remotely controlled robotic diagnosis and examination, surgery, biopsy, and the like in a medical environment (such as a magnetic-resonance machine).

In some embodiments, the present invention includes one or more of any one or more of the devices in any of the figures herein in a combined unit that connects the described variable components, optionally including other conventional components.

Some embodiments further include an automatic parameter-adjustment unit operatively coupled to the LC circuit and configured to adjust electrical parameters of the LC circuit to control the resonance frequency of the LC circuit.

Some embodiments further include an automatic parameter-adjustment unit that has a non-magnetic mechanical actuator operatively coupled to the LC circuit and configured to adjust electrical parameters of the LC circuit to control the resonance frequency of the LC circuit.

In some embodiments, the present invention provides a method that includes: providing a case having an LC circuit that is mounted to the case and that has a resonance frequency at a frequency of RF signals carried on the at least one inner conductor; a piercing structure electrically connected to the LC circuit and configured to pierce and electrically connect the LC circuit to the shield conductor of the shielded RF cable; and an attachment device configured to hold the case to the shielded RF cable with the LC circuit electrically connected to the shield conductor of the shielded RF cable.

Some embodiments further include automatically adjusting electrical parameters of the LC circuit to adjust the resonance frequency.

Some embodiments further include automatically adjusting electrical parameters of the LC circuit to adjust the resonance frequency by moving a non-magnetic mechanical-movement device.

In some embodiments of the method, the plurality of projections electrically connected to the LC circuit include a first plurality of pointed projections at a first end of the case and a second plurality of pointed projections at a second end of the case opposite the first.

In some embodiments of the method, the plurality of projections electrically connected to the LC circuit include a first plurality of pointed projections at a first end of the case and a second plurality of pointed projections at a second end of the case opposite the first, wherein each one of the first plurality of pointed projections is capacitively coupled to a cylindrical conductor spaced apart from the shield conductor of the shielded RF cable, and wherein each one of the second plurality of pointed projections is capacitively coupled to the cylindrical conductor.

In some embodiments of the method, the plurality of projections electrically connected to the LC circuit include a first plurality of pointed projections only at a first end of the case and no pointed projections at a second end of the case opposite the first, and the LC circuit includes a conductive cylinder that is electrically connected to first plurality of pointed projections only at a first end of the case.

In some embodiments of the method, the LC circuit includes a plurality of pi networks arranged at different radial directions around the shielded RF cable.

In some embodiments, the LC circuit includes a plurality of Tee networks arranged at different radial directions around the shielded RF cable.

In some embodiments of the method, the LC circuit includes a plurality of quad-coupler networks arranged at different radial directions around the shielded RF cable.

In some embodiments of the method, the LC circuit includes a plurality of Wilkenson power-splitter-combiner networks arranged at different radial directions around the shielded RF cable.

In some embodiments of the method, the LC circuit includes a plurality of rat-race-coupler networks arranged at different radial directions around the shielded RF cable.

In some embodiments, the present invention provides a radially attachable RF trap attached from a side to a shielded RF cable. In some embodiments, the RF trap creates a high impedance on the outer shield of the RF cable at a frequency of RF signals carried on at least one inner conductor of the cable. In some embodiments, an RF-trap apparatus for blocking stray signals on a shielded RF cable that has a peripheral shield conductor and a inner conductor for carrying RF signals includes: a case; an LC circuit having a resonance frequency equal to RF signals carried on the inner conductor; projections that pierce and connect the LC circuit to the shield conductor; and an attachment device that holds the case to the cable with the LC circuit electrically connected to the shield conductor of the shielded RF cable.

In some embodiments, the present invention provides a non-transitory computer-readable medium having instructions stored thereon for causing a suitably programmed information processor to execute a method that comprises: autocontrolling an electrical parameter of an LC circuit that is mounted to a case of a snap-on balun attached to a shielded RF cable that has a peripheral shield conductor and at least one inner conductor for carrying RF signals, wherein the LC circuit has a resonance frequency at a frequency of RF signals carried on the at least one inner conductor, wherein the case includes a piercing structure electrically connected to the LC circuit and configured to pierce and electrically connect the LC circuit to the shield conductor of the shielded RF cable.

In some embodiments of the computer-readable medium, the method further includes using a feedback signal operatively coupled to the programmable information-processing device to provide feedback control in order to maintain the electrical parameter of the LC circuit.

In some embodiments of the computer-readable medium, the method further includes controlling resistance, inductance and capacitance (RLC) values of the LC circuit.

In some embodiments, the present invention provides an apparatus for holding a patient in a magnetic-resonance imager (MRI) system. This apparatus includes: a first MRI-compatible earpiece assembly, the first earpiece assembly including a rod connected to a head coil by a first lockable ball joint and an earpiece connected to a proximal end of the rod by a second ball joint, wherein the rod is moveably positioned to a selected one of a plurality of possible pitch and yaw angle combinations of the rod relative to the head coil and to a selected one of a plurality of insertion depths relative to the head coil, and then the first ball joint is configured to be tightened to yieldably hold the rod at the selected pitch angle, yaw angle and insertion depth.

In some embodiments, the apparatus further includes: the head coil; and a second MRI-compatible earpiece assembly, wherein the second MRI-compatible earpiece assembly is substantially similar to the first MRI-compatible earpiece assembly but mirror-symmetric to the first MRI-compatible earpiece assembly about a central plane of the head coil, and wherein the first and the second MRI-compatible earpiece assemblies are attached to the head coil by their respective first ball joints.

In some embodiments of the apparatus, the first and the second MRI-compatible earpiece assemblies each include an audio transducer configured to deliver audio content to a patient in the head coil.

In some embodiments of the apparatus, at least one of the earpiece assemblies includes one or more RF coils for transmitting RF MRI signals.

In some embodiments of the apparatus, at least one of the earpiece assemblies includes one or more RF coils for receiving RF MRI signals.

In some embodiments of the apparatus, at least one of the earpiece assemblies includes one or more RF coils for both transmitting and receiving RF MRI signals.

In some embodiments of the apparatus, the first earpiece assembly includes one or more RF coils for both transmitting and receiving RF MRI signals.

In some embodiments of the apparatus, the first earpiece assembly includes one or more RF coils for transmitting RF MRI signals.

In some embodiments of the apparatus, the first earpiece assembly includes one or more RF coils for receiving RF MRI signals.

In some embodiments, the present invention provides a method for holding a patient in a magnetic-resonance imager (MRI) system, the method comprising: providing a first MRI-compatible earpiece assembly, the first earpiece assembly including a rod connected to a head coil by a first lockable ball joint and an earpiece connected to a proximal end of the rod by a second ball joint; positioning the first MRI-compatible earpiece to a selected one of a plurality of possible pitch and yaw angle combinations of the rod relative to the head coil and to a selected one of a plurality of insertion depths relative to the head coil; and tightening the first ball joint to yieldably hold the rod at the selected pitch angle, yaw angle, and insertion depth.

Some embodiments of the method further include providing the head coil, and a second MRI-compatible earpiece assembly, wherein the second MRI-compatible earpiece assembly is substantially similar to the first MRI-compatible earpiece assembly but mirror-symmetric to the first MRI-compatible earpiece assembly about a central plane of the head coil, and attaching the first and the second MRI-compatible earpiece assemblies to the head coil by their respective first ball joints.

Some embodiments of the method further include delivering audio content to a patient in the head coil through the first and the second MRI-compatible earpiece assemblies.

Some embodiments of the method further include transmitting RF MRI signals from the first earpiece assembly.

Some embodiments of the method further include receiving RF MRI signals from the first earpiece assembly.

Some embodiments of the method further include transmitting and receiving RF MRI signals from the first earpiece assembly.

In some embodiments, the present invention provides an apparatus for imaging a patient in a magnetic-resonance imager (MRI) system. This apparatus includes: a first MRI-compatible positionable patient-interface assembly, the first assembly including a positioning rod configured to be connected to a frame by a first lockable joint and a housing connected to a proximal end of the rod by a second joint, wherein the rod is moveably positioned to a selected one of a plurality of possible pitch-and-yaw-angle combinations of the rod relative to the frame and to a selected one of a plurality of insertion depths relative to the frame, and wherein the first joint is configured to be tightened to yieldably hold the rod at the selected pitch angle, yaw angle and insertion depth.

Some embodiments further include the frame, wherein the frame includes a coil frame with a coil; and a second MRI-compatible positionable patient-interface assembly, wherein the second assembly is substantially similar to the first assembly but minor-symmetric to the first assembly about a central plane of the coil frame, and wherein the first and the second MRI-compatible assemblies are attached to the coil frame by their respective first joints.

In some embodiments, the first positionable assembly includes a fluid circulation passageway configured to circulate a fluid within the first positionable assembly to control a temperature of a patient.

In some embodiments, the first patient-interface assembly includes one or more RF coils to both transmit and receive RF MRI signals.

In some embodiments, the first patient-interface assembly includes a motor interfaced to the positioning rod to controllably extend and withdraw and end of the positionable patient-interface assembly.

In some embodiments, the first patient-interface assembly includes one or more skin-contact electrodes configured to receive electrical signals from a tissue of a patient and conduct the signals through the positioning rod.

In some embodiments, the first patient-interface assembly includes one or more liquid-delivery tubes configured to deliver a liquid to a patient through the positioning rod.

In some embodiments, the first patient-interface assembly includes one or more gas-delivery tubes configured to deliver a gas to a patient through the positioning rod.

In some embodiments, the first patient-interface assembly includes a plurality of RF cables for both transmitting and receiving RF MRI signals through the positioning rod.

In some embodiments, the present invention provides a method for imaging a patient in a magnetic-resonance imager (MRI) system. This method includes: providing a first MRI-compatible patient-interface assembly, the first patient-interface assembly including a rod that is connected to a frame by a first lockable joint and an patient interface connected to a proximal end of the rod by a second joint; positioning the first MRI-compatible patient-interface to a selected one of a plurality of possible pitch-and-yaw-angle combinations of the rod relative to the frame and to a selected one of a plurality of insertion depths relative to the frame; and tightening the first joint to yieldably hold the rod at the selected pitch angle, yaw angle, and insertion depth.

Some embodiments of the method further include providing the frame, wherein the frame holds a coil, providing a second MRI-compatible patient-interface assembly, wherein the second MRI-compatible patient-interface assembly is substantially similar to the first MRI-compatible patient-interface assembly but minor-symmetric to the first MRI-compatible patient-interface assembly about a central plane of the coil, and attaching the first and the second MRI-compatible patient-interface assemblies to the coil by their respective first joints.

Some embodiments of the method further include delivering audio content to a patient in the coil through the first and the second MRI-compatible patient-interface assemblies.

Some embodiments of the method further include transmitting RF MRI signals from the first patient-interface assembly.

Some embodiments of the method further include receiving RF MRI signals by the first patient-interface assembly.

Some embodiments of the method further include transmitting and receiving RF MRI signals from the first patient-interface assembly.

In some embodiments, the present invention provides an apparatus for imaging a patient in a magnetic-resonance imager (MRI) system. This apparatus includes: a frame configured to be positioned in a bore of an MRI magnet of the MRI system; and a first MRI-compatible patient-interface assembly, the first patient-interface assembly including a patient-interface positioner configured to be connected to a reference position on the frame; a first lockable joint on the positioner; and a patient interface connected to a proximal end of the positioner by a second joint on the positioner, wherein the first patient interface is moveably positioned to a selected pitch angle and a selected yaw angle of a plurality of possible pitch-and-yaw-angle combinations of the patient interface relative to the reference position on the frame and to a selected one of a plurality of distances relative to the reference position on the frame, and wherein the first lockable joint is configured to be tightened to yieldably hold the first patient interface at the selected pitch angle, the selected yaw angle, and the selected one of the plurality of distances, relative to the reference position on the frame.

In some embodiments, the frame includes a coil frame with a coil; and a second MRI-compatible patient-interface assembly, wherein the second MRI-compatible patient-interface assembly is substantially similar to the first MRI-compatible patient-interface assembly, and wherein the first and the second MRI-compatible patient-interface assemblies are attached to the coil frame by their respective first lockable joints.

In some embodiments, the first and the second MRI-compatible patient-interface assemblies each include an audio transducer configured to deliver audio content to a patient in the coil.

In some embodiments, the first patient-interface assembly includes one or more RF coils for transducing RF MRI signals.

In some embodiments, the first patient-interface assembly includes a motor interfaced to the positioning rod to controllably extend and withdraw and end of the positionable patient-interface assembly.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first, " "second," and "third," etc., are used merely as labels, and are not intended to impose numerical requirements on their objects.

What is claimed is:

1. An apparatus comprising:
   a frame;
   a first positionable patient-interface assembly, the first patient-interface assembly including:
      a positioning rod, wherein the positioning rod has a proximal end and a distal end;
      a housing;
      a first lockable joint assembly connected to the frame, wherein the first lockable joint assembly is configured to be loosened and tightened;
      a second joint, wherein the positioning rod is configured to be connected to the frame by the first lockable joint assembly, wherein the housing is connected to the proximal end of the rod by the second joint, wherein the rod passes through the first lockable joint assembly and is configured to be moveably positioned to a selected one of a plurality of possible pitch-and-yaw-angle combinations of the rod relative to the frame and to a selected one of a plurality of insertion depths relative to the frame, and wherein the first lockable joint assembly is configured to be tightened to yieldably hold the rod at the selected pitch angle, yaw angle and insertion depth.

2. The apparatus of claim 1, wherein the first positionable patient-interface assembly is MRI compatible, wherein the frame includes a coil frame with an RF coil; and wherein the apparatus further comprises:
   a second MRI-compatible positionable patient-interface assembly, wherein the second patient-interface assembly is substantially similar to the first patient-interface assembly but mirror-symmetric to the first patient-interface assembly about a central plane of the coil frame, and wherein the first and the second MRI-compatible patient-interface assemblies are attached to the coil frame by their respective first joints.

3. The apparatus of claim 1, wherein the first positionable patient-interface assembly includes a fluid circulation passageway configured to circulate a fluid within the first positionable patient-interface assembly to control a temperature of at least a portion of a patient.

4. The apparatus of claim 1, wherein the first positionable patient-interface assembly is MRI compatible, wherein the frame includes a coil frame with an RF coil; and wherein the RF coil is configured to both transmit and receive RF MRI signals.

5. The apparatus of claim 1, wherein the first patient-interface assembly includes a motor interfaced to the positioning rod to controllably extend and withdraw an end of the first patient-interface assembly.

6. The apparatus of claim 1, wherein the first patient-interface assembly includes one or more skin-contact electrodes configured to receive electrical signals from a tissue of a patient and conduct the signals through the positioning rod.

7. The apparatus of claim 1, wherein the first patient-interface assembly includes one or more liquid-delivery tubes configured to deliver a liquid to a patient through the positioning rod.

8. The apparatus of claim 1, wherein the first patient-interface assembly includes one or more gas-delivery tubes configured to deliver a gas to a patient through the positioning rod.

9. The apparatus of claim 1, wherein the first patient-interface assembly includes a plurality of RF cables for both transmitting and receiving RF MRI signals through the positioning rod.

10. The apparatus of claim 1, wherein the first lockable joint assembly includes a first tightening mechanism that locks the selected one of the plurality of pitch-and-yaw-angle combinations, and a second tightening mechanism that locks the selected one of the plurality of insertion depths.

11. The apparatus of claim 1, wherein the first patient-interface assembly further includes:
an RF coil; and
a power amplifier located within the first patient-interface assembly and operably coupled to receive a first transmit signal and to supply an amplified version of the first transmit signal to the RF coil.

12. The apparatus of claim 1, wherein the first patient-interface assembly further includes:
an RF coil;
a power amplifier located within the first patient-interface assembly and operably coupled to receive a first transmit signal and to supply an amplified version of the first transmit signal to the RF coil; and
a preamplifier located within the first patient-interface assembly and operably coupled to pre-amplify a receive signal received by the RF coil.

13. The apparatus of claim 1, wherein the apparatus further comprises:
a second MRI-compatible positionable patient-interface assembly, wherein the second patient-interface assembly is substantially similar to the first patient-interface assembly but mirror-symmetric to the first patient-interface assembly about a central plane of the frame, wherein the first and the second patient-interface assemblies are attached to the frame by their respective first joints, wherein the first lockable joint assembly of the second patient-interface assembly includes a first tightening mechanism that locks the selected one of the plurality of pitch-and-yaw-angle combinations of the second interface assembly, and a second tightening mechanism that locks the selected one of the plurality of insertion depths of the second interface assembly.

14. An apparatus comprising:
a frame;
a first patient-interface assembly, the first patient-interface assembly including:
a rod connected to the frame, wherein the rod has a proximal end and a distal end;
a housing connected to the proximal end of the rod;
means for connecting the housing to the proximal end of the rod; and
means for positioning the rod to a selected one of a plurality of possible pitch-and-yaw-angle combinations of the rod relative to the frame and to a selected one of a plurality of insertion depths relative to the frame, wherein the means for positioning is configured to be tightened to yieldably hold the rod at the selected pitch angle, yaw angle, and insertion depth.

15. The apparatus of claim 14, wherein the first patient-interface assembly further includes:
means for locking the selected one of the plurality of pitch-and-yaw-angle combinations; and
means for locking the selected one of the plurality of insertion depths.

16. The apparatus of claim 14, wherein the first patient-interface assembly further includes:
an RF coil;
means for receiving a first transmit signal and supplying an amplified version of the first transmit signal to the RF coil; and
means for pre-amplifying a receive signal received by the RF coil.

17. The apparatus of claim 14, wherein the first patient-interface assembly further includes means for outputting sound to the patient.

18. The apparatus of claim 14, wherein the first patient-interface assembly further includes means for circulating a fluid within the first patient-interface assembly to control a temperature of at least a portion of a patient.

19. The apparatus of claim 14, wherein the first patient-interface assembly further includes means for controllably extending and withdrawing an end of the first patient-interface assembly.

20. An apparatus comprising:
a frame;
a first positionable patient-interface assembly, the first patient-interface assembly including:
a positioning rod;
a patient-interface housing;
a first lockable joint assembly connected to the frame, wherein the first lockable joint assembly is configured to be loosened and tightened;
a second joint, wherein the patient-interface housing is connected to a proximal end of the rod by the second joint, wherein the rod is moveably positionable to a selected one of a plurality of possible pitch-and-yaw-angle combinations of the rod relative to the frame and to a selected one of a plurality of insertion depths relative to the frame, and wherein the first joint assembly is configured to be tightened to yieldably hold the rod at the selected pitch angle, yaw angle and insertion depth relative to the frame.

* * * * *

UNITED STATES PATENT AND TRADEMARK OFFICE
CERTIFICATE OF CORRECTION

PATENT NO. : 9,820,676 B2
APPLICATION NO. : 14/548276
DATED : November 21, 2017
INVENTOR(S) : Brandon J. Tramm et al.

Page 1 of 1

It is certified that error appears in the above-identified patent and that said Letters Patent is hereby corrected as shown below:

In the Specification

In Column 1, Lines 12-13:
Delete "(which issued as U.S. Pat. No. 9,700,232 on Jul. 11, 2017)".

In the Claims

In Column 18, Line 36 (Line 3 of Claim 17):
Delete "sound to the patient." and insert -- sound to a patient. -- therefor.

Signed and Sealed this
Nineteenth Day of December, 2017

Joseph Matal
*Performing the Functions and Duties of the
Under Secretary of Commerce for Intellectual Property and
Director of the United States Patent and Trademark Office*